(12) United States Patent
Dykes

(10) Patent No.: US 11,147,544 B2
(45) Date of Patent: Oct. 19, 2021

(54) INTRAOCULAR EXPANSION AND RETENTION METHODS

(71) Applicant: Ronald Dykes, The Woodlands, TX (US)

(72) Inventor: Ronald Dykes, The Woodlands, TX (US)

( * ) Notice: Subject to any disclaimer, the term of this patent is extended or adjusted under 35 U.S.C. 154(b) by 319 days.

(21) Appl. No.: 16/454,818

(22) Filed: Jun. 27, 2019

(65) Prior Publication Data

US 2019/0314010 A1  Oct. 17, 2019

Related U.S. Application Data

(60) Division of application No. 14/956,701, filed on Dec. 2, 2015, now Pat. No. 10,357,235, which is a continuation of application No. 14/308,414, filed on Jun. 18, 2014, now abandoned.

(60) Provisional application No. 62/086,670, filed on Dec. 2, 2014, provisional application No. 61/837,099, filed on Jun. 19, 2013.

(51) Int. Cl.
*A61B 17/02* (2006.01)
*A61F 9/00* (2006.01)

(52) U.S. Cl.
CPC ...... *A61B 17/0231* (2013.01); *A61B 17/0293* (2013.01); *A61F 9/0017* (2013.01)

(58) Field of Classification Search
CPC .................. A61B 17/0231; A61B 17/0293; A61F 9/0017
See application file for complete search history.

(56) References Cited

U.S. PATENT DOCUMENTS

| | | |
|---|---|---|
| 3,925,825 A | 12/1975 | Richards |
| 3,979,780 A | 9/1976 | Boniuk |
| 4,321,916 A | 3/1982 | McKee |
| 4,387,706 A | 6/1983 | Glass |
| 4,428,746 A | 1/1984 | Mendez |
| 5,163,419 A | 11/1992 | Goldman |
| 5,267,553 A | 12/1993 | Graether |
| 5,318,011 A | 6/1994 | Federman et al. |
| 5,322,054 A | 6/1994 | Graether |
| 6,083,155 A | 7/2000 | Trese |
| 6,183,480 B1 | 2/2001 | Mackool |
| 6,497,724 B1 | 12/2002 | Stevens et al. |
| 6,620,098 B1 | 9/2003 | Milverton |
| 7,175,594 B2 | 2/2007 | Foulkes |
| 7,806,929 B2 | 10/2010 | Brown |
| 7,947,049 B2 | 5/2011 | Vaquero |
| 7,985,180 B2 | 7/2011 | Brown |
| 8,323,296 B2 | 12/2012 | Malyugin |

(Continued)

*Primary Examiner* — Samuel S Hanna
(74) *Attorney, Agent, or Firm* — Shackelford, Bowen, McKinley & Norton, LLP; Henry L. Ehrlich

(57) ABSTRACT

An exemplary method for expanding and maintaining an intraocular opening includes compressing along an axis a circular body comprising a first pocket, a second pocket, a third pocket and a fourth pocket positioned vertically below a top band section. Inserting intraocular tissue of an eye in the first pocket of the compressed circular body, thereby elongating the intraocular opening, and inserting the intraocular tissue in the second pocket and the third pocket as the body decompresses. Decompressing the body and inserting the intraocular tissue in the fourth pocket thereby expanding the intraocular opening.

19 Claims, 13 Drawing Sheets

(56) References Cited

U.S. PATENT DOCUMENTS

| | | |
|---|---|---|
| 8,376,743 B1 | 2/2013 | Buckhary |
| 8,496,583 B1 | 7/2013 | Reynard |
| 8,876,859 B2 | 11/2014 | Buehler et al. |
| 8,900,136 B2 | 12/2014 | Cote et al. |
| D735,857 S | 8/2015 | Dykes |
| 2003/0092970 A1 | 5/2003 | Lee |
| 2013/0053860 A1 | 2/2013 | Malyugin |
| 2014/0221759 A1* | 8/2014 | Mackool ............ A61B 17/0231 600/209 |

\* cited by examiner

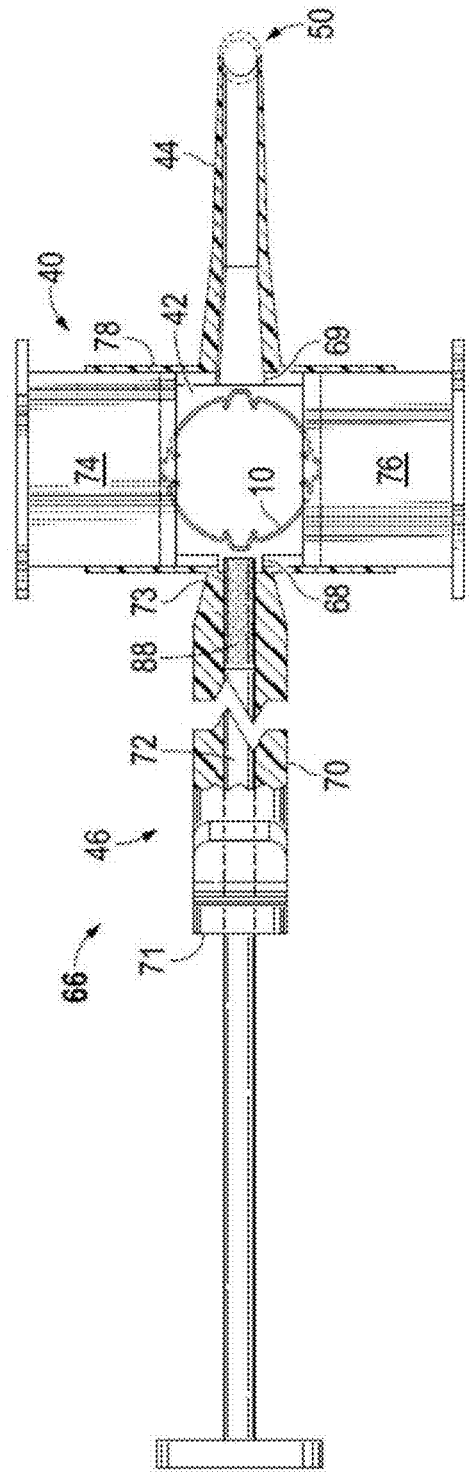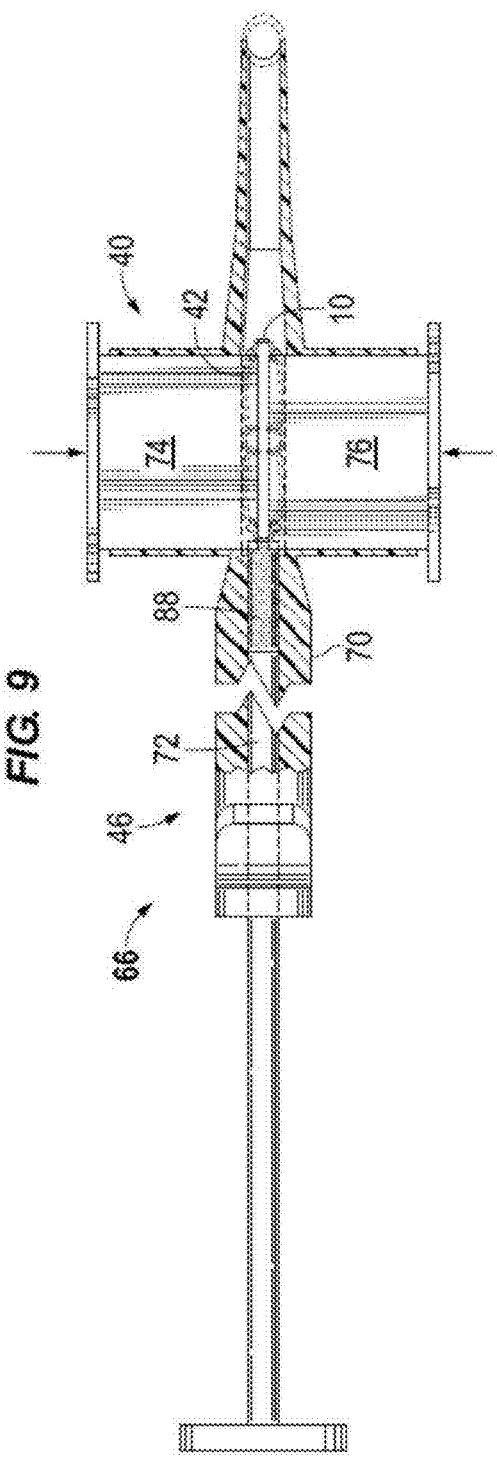

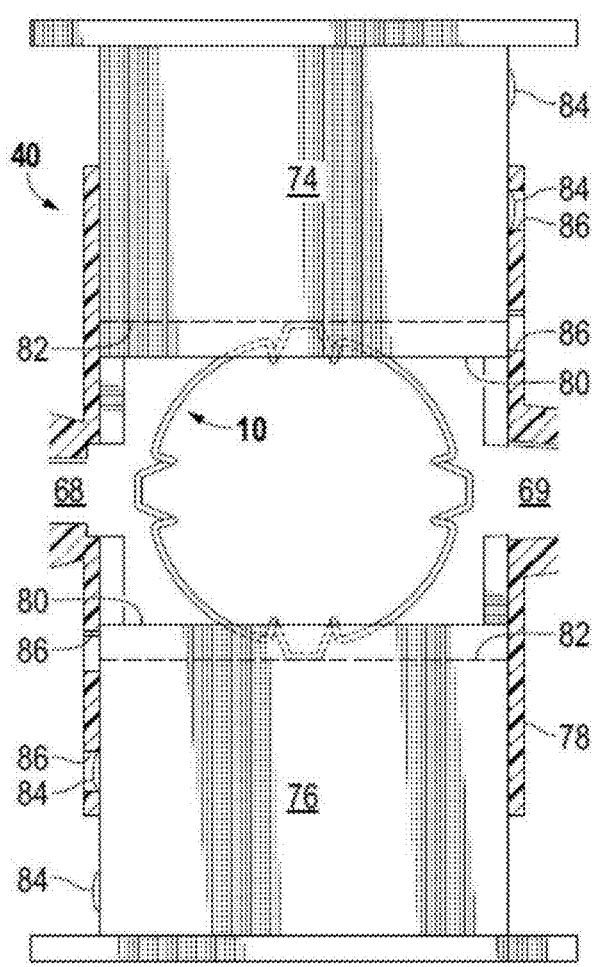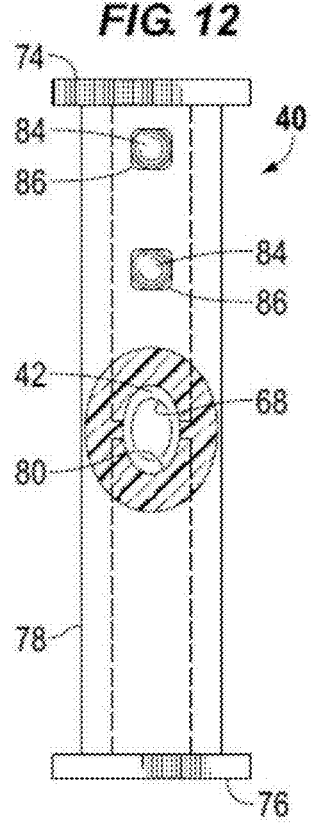

INTRAOCULAR EXPANSION AND RETENTION METHODS

BACKGROUND

This section provides background information to facilitate a better understanding of the various aspects of the disclosure. It should be understood that the statements in this section of this document are to be read in this light, and not as admissions of prior art.

There are various intraocular surgical procedures that require the iris be dilated in order to better visualize the surgical field, including cataract extraction. Cataract extraction is the primary intraocular surgical procedure performed today. The surgical outcome for this procedure is greatly enhanced when performed through a well dilated pupil. There are other methods of cataract extraction being performed today with femtosecond laser being one method. Having a well dilated pupil enhances surgical outcomes in phacoemulsification but is mandatory in performing femtosecond laser surgery.

SUMMARY

In accordance to one or more aspects of the disclosure, a device is provided to expand and maintain an intraocular opening in an expanded position during an intraocular procedure includes a body forming a central opening, the body having a top band and spaced apart stepped blades. Each of the stepped blades forms an outwardly facing pocket to receive intraocular tissue and the top band forming a gap above each of the pockets.

A method according to one or more embodiments includes compressing along an axis a circular body comprising a first pocket, a second pocket, a third pocket and a fourth pocket positioned vertically below a top band section. Inserting intraocular tissue of an eye in the first pocket of the compressed circular body, thereby elongating an intraocular opening, and inserting the intraocular tissue in the second pocket and the third pocket as the body decompresses. Decompressing the body and inserting the intraocular tissue in the fourth pocket thereby expanding the intraocular opening. In accordance with some embodiments, the decompressed circular body has an inside diameter for example across points of fixation of greater than about 6 mm and in some embodiments greater than about 7 mm. The circular body providing an expansion force to bias the body to a decompressed circular shape.

An exemplary method includes compressing a circular circuitous body having a central opening with a center, a top band extending along a plane, and a first pocket, a second pocket, a third pocket, and a fourth pocket positioned vertically below the plane, wherein the pockets are equally spaced around the circular circuitous body, each of the pockets comprising the circuitous body extending inward from opposing top compression bends located at the top band toward the center to opposing top height bends, the circuitous body extending downward along legs, located radially inside of the top band, from the opposing top height bends to opposing bottom height bends, the circuitous body extending outward away from the center along feet from the opposing bottom height bends to opposing bottom compression bend, a front edge portion of the circuitous body connecting the opposing bottom compression bends, an inside diameter across the legs, an outside diameter across the top band, wherein the outside diameter is greater than the inside diameter, and an open gap in the plane between the opposing top height bends vertically above each of the pockets; inserting intraocular tissue in the first pocket of the compressed circuitous body; inserting the intraocular tissue into the second pocket and the third pocket of the compressed circuitous body, wherein the second and third pockets are located circumferentially opposite one another; decompressing the circuitous body into a circular shape before inserting the intraocular tissue in the fourth pocket; and inserting the intraocular tissue in the fourth pocket thereby expanding an opening in the intraocular tissue.

The foregoing has outlined some of the features and technical advantages in order that the detailed description that follows may be better understood. Additional features and advantages will be described hereinafter which form the subject of the claims of the invention. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

FIGS. 8-10 illustrate an exemplary intraocular expansion and retention device injection and cartridge system in accordance to one or more embodiments.

FIG. 11 illustrates a top view of an exemplary cartridge of injection and cartridge system in accordance to one or more embodiments.

FIG. 12 is a side view of an exemplary cartridge of injection and cartridge system in accordance to one or more embodiments.

DETAILED DESCRIPTION

Figure 1:
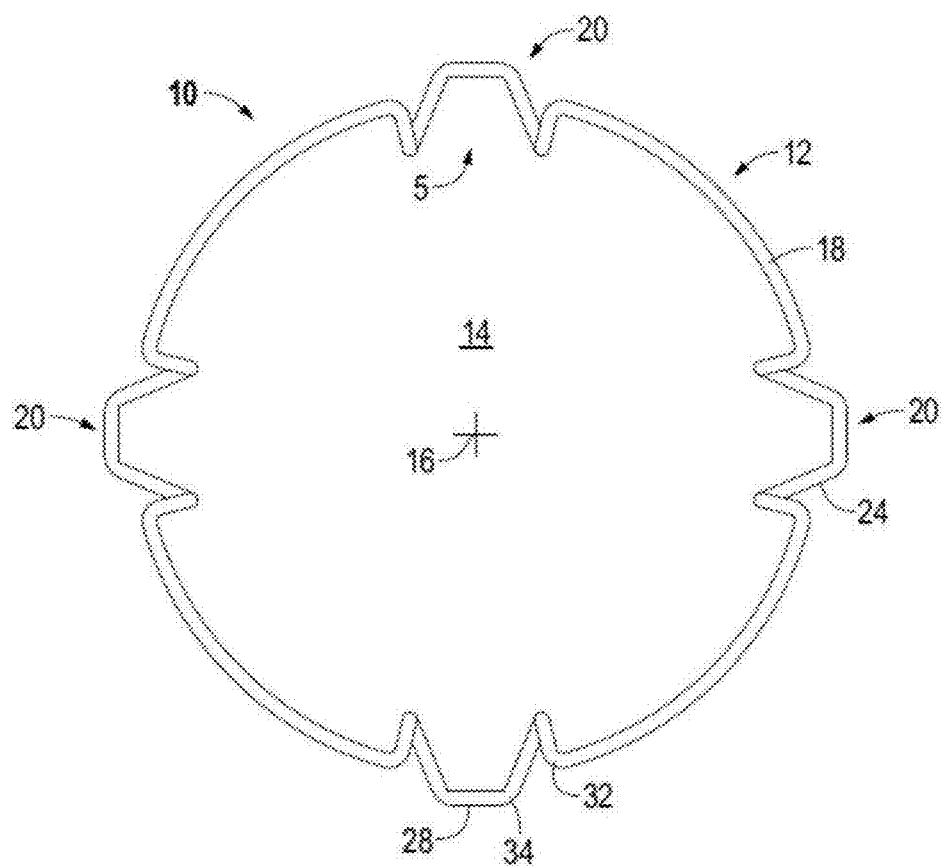
FIGS. 1 and 1A illustrate top views of an exemplary decompressed intraocular expansion and retention devices in accordance to one or more embodiments.

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

Disclosed is an intraocular expansion and retention device ("IERD") 10 that expands the iris enlarging the pupillary space (pupil) during intraocular surgery and is removed following the procedure. Intraocular expansion and retention device 10 includes a number of stepped blades that engage the iris margins at points of fixation, or contact, expanding the pupil and allowing increased visualization during intraocular surgery. In accordance with aspects of the disclosure, IERD 10 may dilate a pupil greater than 7 millimeters. IERD 10 allows patients with small pupils to have access to this latest technology in cataract surgery. It acts as a stabilizer in helping to maintain the position of the iris during intraocular procedures such as cataract extraction. Once removed, the iris returns to its normal size and shape reforming the pupil. In accordance to some embodiments, intraocular expansion and retention device 10 engages the margins of a capsulorhexis to retain and stabilize the capsule during cataract extraction procedures where zonular dehiscence, pseudo exfoliation or other indicators for use are present.

IERD 10 expands the pupil without damaging the delicate intraocular structures of the eye, including the iris and the cornea, during insertion, placement and removal. It is also beneficial in that it creates a circular opening that more closely emulates the natural state of a dilated pupil. IERD 10 addresses both of these criteria by creating a larger circular viewing area with multiple points of fixation, while gently expanding the iris without wedging the iris between two surfaces, incorporating a predetermined amount of compression resistance so as not to damage the tissue but enough to expand and retain the tissue. IERD 10 also allows for atraumatic removal in that it collapses for easy extraction.

In accordance to one or more embodiments, IERD 10 expands the pupillary space during an ophthalmic procedure by gently cradling the iris margins while applying equal compression resistance. This creates an expanded concentric opening of the pupil, enhancing surgical outcomes by significantly increasing visualization of the surgical site. In accordance to one or more embodiments, IERD 10 disclosed herein can expand the pupil up to 8 mm while retaining a substantially circular opening. IERD 10 is less traumatic then other expansion devices in that it cradles the iris margins and it does not squeeze or pinch the margins. IERD 10 requires minimal surgical maneuvers to disengage the intraocular tissue during removal and is therefore less traumatic.

Figure 1A:
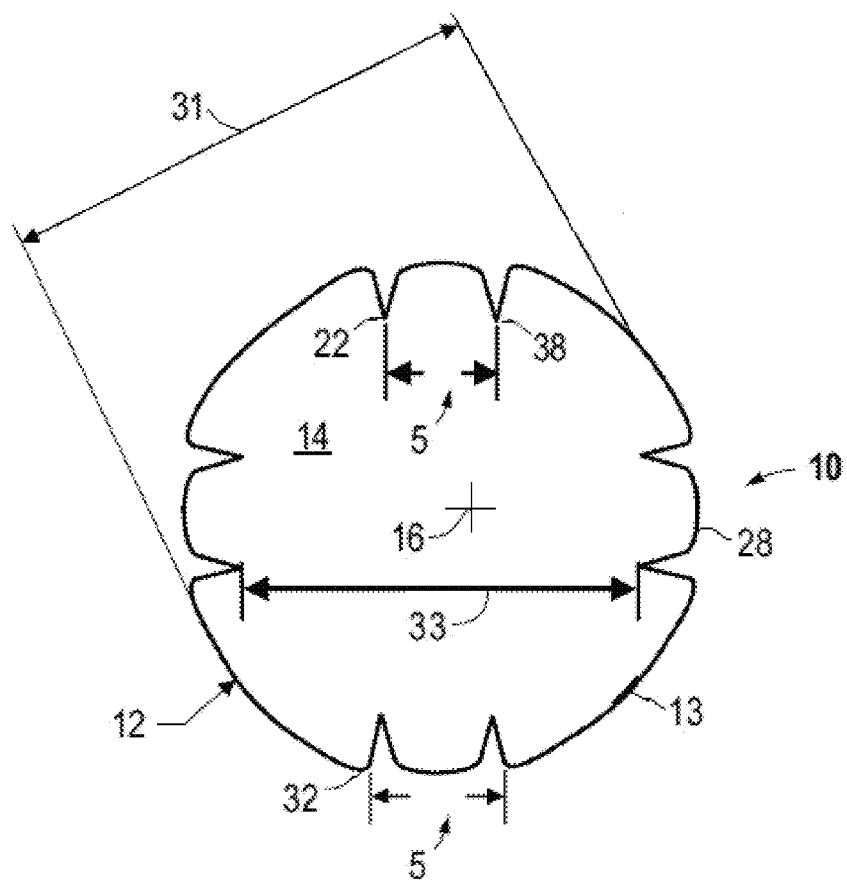

IERD 10 comprises a circuitous member 12 referred to herein as body 12 forming a central opening 14 having a center 16. IERD 10 may be formed for example by molding or forming a material such as, but not limited to, plastic, resins, metal (e.g., nickel and titanium alloy), and carbon fibers. Body 12 may be formed a circuitous configuration as a single continuous piece, as a single piece interconnected (e.g., adhesive, weld) at its opposing ends, or multiple interconnected pieces. For example, in FIG. 1A a single member 12 is connected at its opposing ends by a connector 13 depicted in this example as a weld. In accordance to some embodiments the welded quadrant is equal in length to the other three quadrants. In accordance to an embodiment the connection, for example a weld, can withstand about 50 grams of tension without breaking or stretching.

Circular body 12 comprises a top band section 18 and spaced apart stepped down blades (e.g. loops, shelves, lips) generally denoted by the numeral 20. In accordance to aspects of the disclosure, open paths or gaps 5 (e.g., openings) are formed in top band section 18 above each stepped blade 20. For example, gap 5 is formed in top band section 18 between for example the adjacent top bends 32 and/or top height bends 36 above the outwardly facing pocket that is provided by the stepped blade to receive and cup the iris margin and between the adjacent legs 22 for example at bottom bends 38. The length of the gap may vary between the different portions of the stepped blade. The depicted devices 10 are illustrated with four blades which may be spaced at equal distances from one another. For example, pairs of blades are located circumferentially opposite from one another. Top band section or portion 18 may be configured to substantially emulate the natural shape of a pupil when body 12 is decompressed. The top band portion may act as expansion bands to store energy and in use to expand the iris when the body expands from a compressed state to a decompressed or expanded state.

Figure 2:
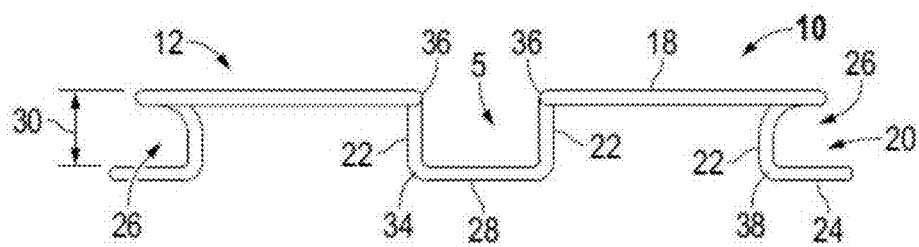
FIGS. 2 and 2A illustrate in elevation an exemplary intraocular expansion and retention devices in accordance to one or more embodiments.
Figure 2A:
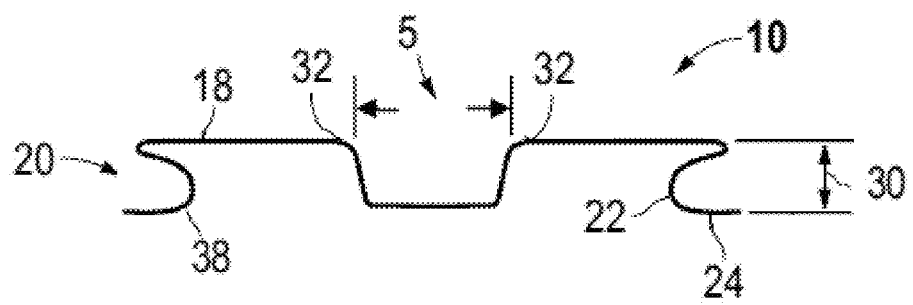
Figure 3:
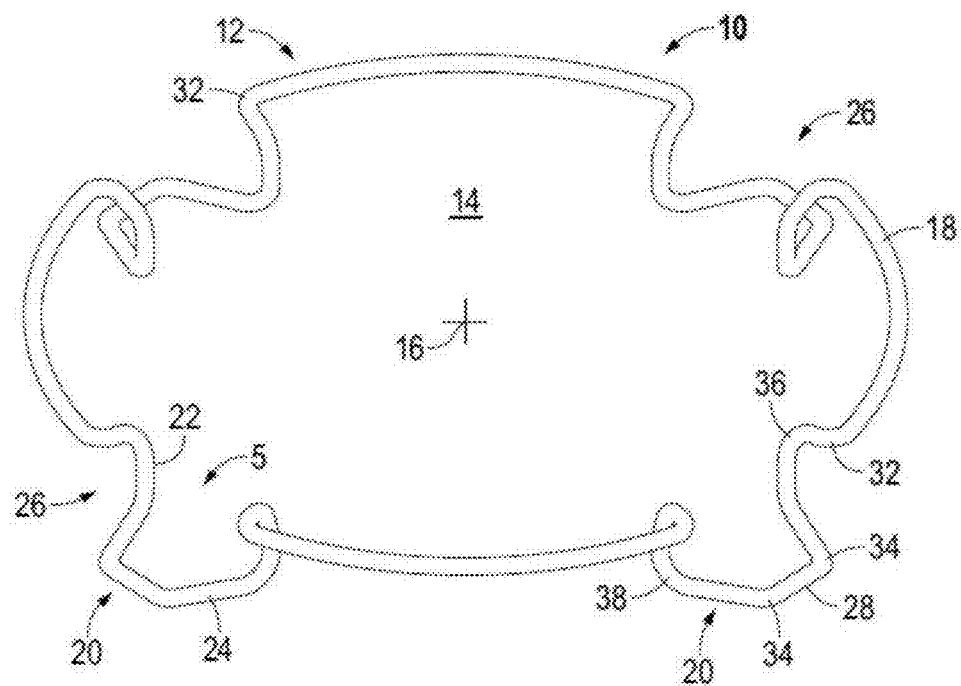
FIG. 3 illustrates in perspective an exemplary intraocular expansion and retention device in accordance to one or more embodiments.
Figure 6:
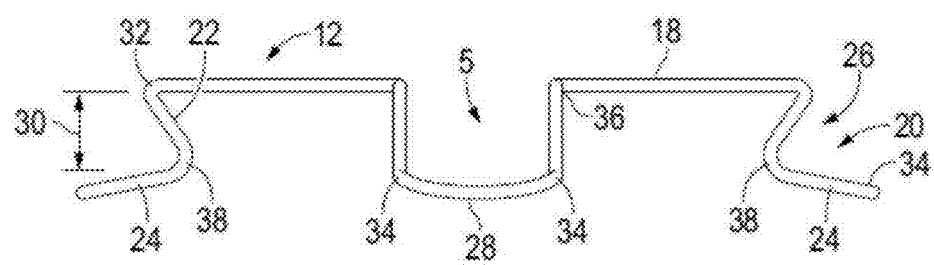
FIG. 6 illustrates in elevation an exemplary intraocular expansion and retention device in accordance to one or more embodiments.
Figure 7:
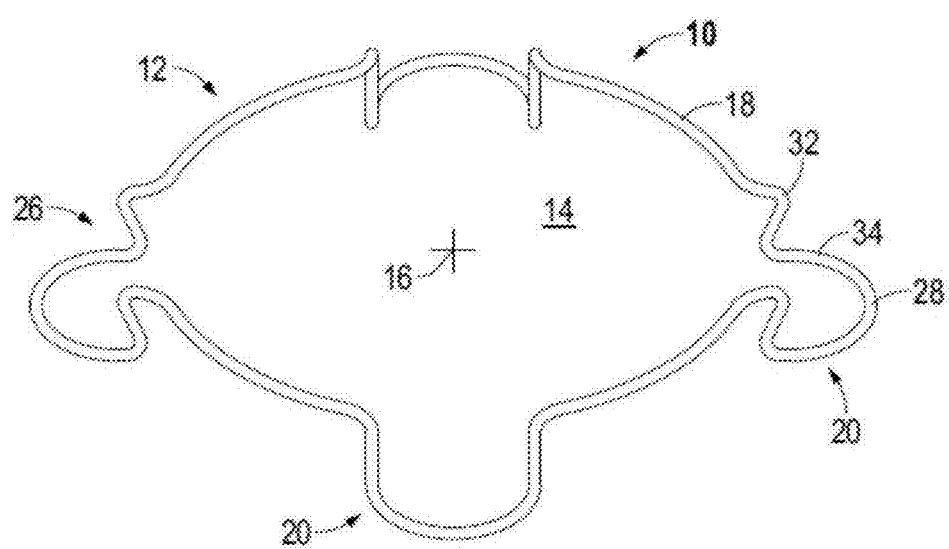
FIG. 7 illustrates in perspective an exemplary intraocular expansion and retention device in accordance to one or more embodiments.

Each blade 20 is formed by legs 22 extending vertically down from top band section 18 to feet 24 which are interconnected along a front edge 28. Feet 24 extend outward from legs 22 relative to central opening 14 and center 16 to form an outwardly facing open receptacle or pocket 26. In use, feet 24 cradle the iris margin or rim and in some embodiments the capsulorhexis margin. Pocket 26 is formed in particular by feet 24 and legs 22 extending below top band portion 18. Pockets 26 are sized to have a height 30 to receive the iris margin or rim without pinching or wedging the iris into the receptacle. For example, the iris margin is cupped in the pocket of the blade. Pockets 26 (i.e., pockets) may take various shapes, for example, C-shaped, V-shaped, and U-Shaped. Feet 24 may extend along a plane that is parallel or substantially parallel to the plane of top band section 18 as illustrated for example in FIGS. 2 and 2A or the top band section and the feet may extend along nonparallel planes as illustrated for example in FIG. 6.

Each blade 20 provides two fixation points or points of contact with the iris tissue. The points of fixation may be provided at the right and left legs 22 of each blade 20. In some embodiments, for example with reference to FIG. 6, the fixation point may be provided and established at bend 38 between leg 22 and foot 24. Accordingly, an IERD 10 having four blades 20 provides eight fixation points to contact the intraocular tissue, see e.g. FIG. 16. More points of contact with tissue reduces iris trauma and promotes creating a circular pupil.

Each stepped blade 20 is formed by multiple bends or radii in body 12 including compression bends that define an expansion force to decompress the body. The expansion force is surpassed to compress and elongate IERD 10. When body 12 is decompressed the compression bends apply the expansion force to expand the body to the decompressed configuration illustrated for example in FIGS. 1, 1A, 3, 5, and 7. The expansion force of the compression bends act to expand iris 62 as shown for example in FIG. 16 and form an enlarged and substantially circular pupil 60. The compression bends or radii may have a determined expansion force. For example, the compression bends may have a determined constant requiring 2+/−0.3 grams of force to decompress the body and the 2+/−0.3 grams of force acting to expand the body and in use to expand the iris. In accordance to one or more embodiments, IERD 10 may be designed to have a compression/expansion force of between about 2.5 grams, or not less than about 2.5 grams, and about 6.5 grams of force.

Figure 4:
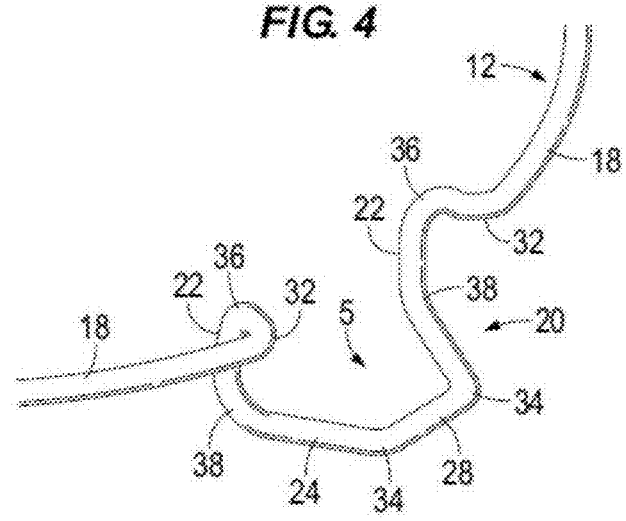
FIG. 4 illustrates an exemplary stepped blade of an intraocular expansion and retention device in isolation in accordance to one or more embodiments.
Figure 5:
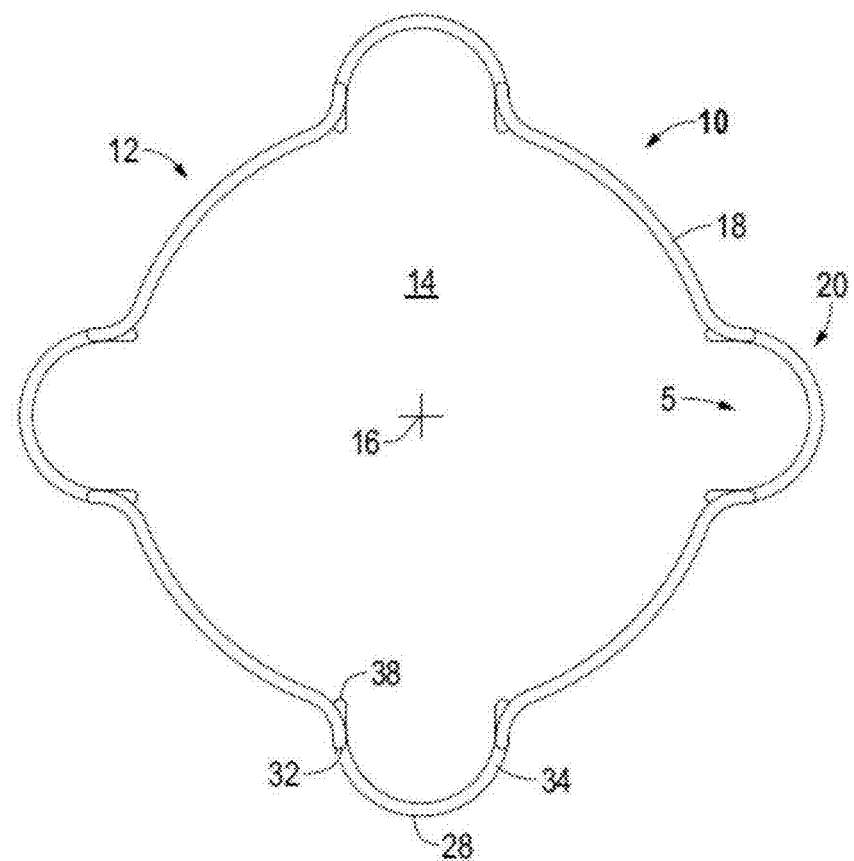
FIG. 5 illustrates a top view of an exemplary decompressed intraocular expansion and retention device in accordance to one or more embodiments.

For example, with reference to in particular to FIG. 4, each blade 20 includes top compression bends 32 and bottom compression bends 34. In the illustrated examples, top band section 18 is turned inward toward the center of the central opening at opposing spaced apart top compression bends 32. Body 12 is then turned downward at top height bends 36 and extends downward at back legs 22 to bottom height bends 38. Body 12 is turned radially outward form the central opening at bottom height bends 38 to the bottom compression bend 34. Front edge 28 portion of body 12 interconnects the opposing, e.g. right and left, bottom compression bends 34 of each blade. Front edge 28 may be a substantially linear length or it may be curved.

Height bends 36 and 38 are positioned to determine the maximum and minimum height of IERD 10 which may be calculated to accommodate and stabilize the iris. Increasing the maximum height may cause the intraocular speculum to become unstable in the eye and cause difficulty in introducing instrumentation into the eye, while exceeding the minimum can pinch or wedge the iris between feet 24 and top band portion 18 causing trauma to the tissue.

Front edge 28 of each blade may extend to or beyond the outside diameter 31 of top band section 18 relative to center 16 when the body is in the decompressed state. Inside diameter 33 (FIG. 1A) of the blades, e.g. across the back of legs 22 may be located radially inside of the inside diameter of top band section 18 when decompressed. In accordance with aspects of the disclosure, in the decompressed state the inside diameter of device 10 is approximately 7 mm. In accordance to one or more aspects, the inside diameter of IERD 10 is greater than 7 mm. In accordance to one or more aspects, the inside diameter of IERD 10 is about 8 mm, equal to 8 mm, or greater than 8 mm. In accordance to an embodiment, the inside diameter is between about 6 mm and 7 mm. In accordance to an embodiment, the inside diameter is about 6.7 mm plus or minus ten percent. For example, with reference to FIG. 17, pupil opening 60 has a diameter greater than the inside diameter of IERD 10 as measured along legs 22, e.g. the points of fixation.

Figure 10:
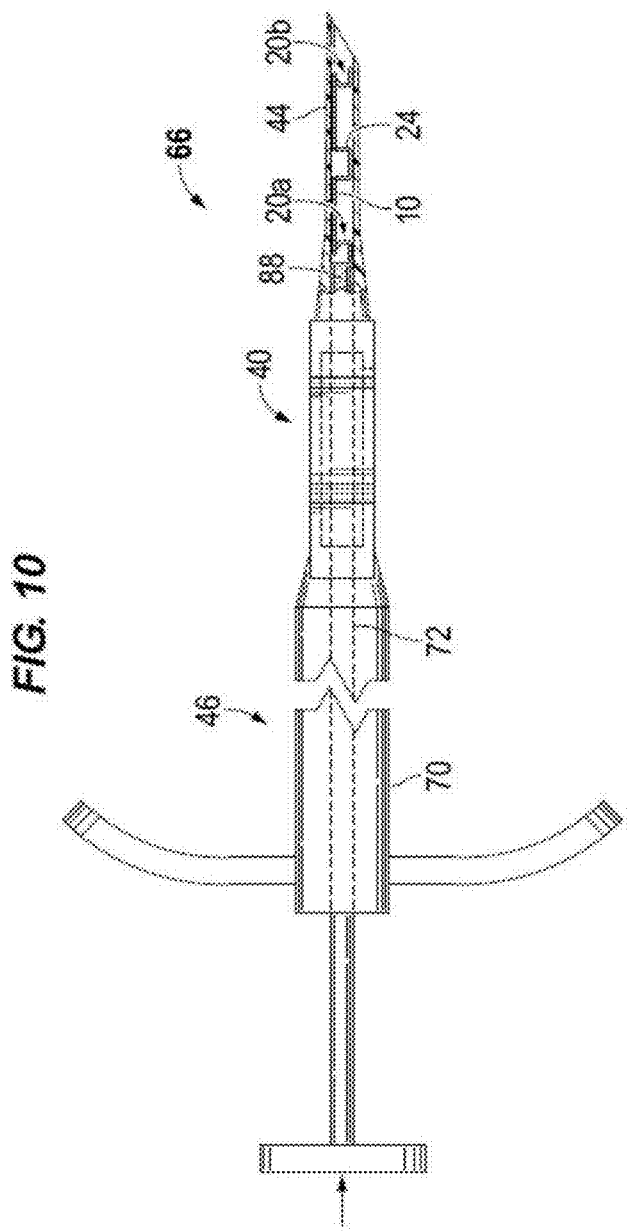

Refer now to FIGS. 8-10, which illustrate an example of a cartridge and injector system 66 utilized with an IERD 10 and FIGS. 11 and 12, which illustrate a cartridge 40 in isolation. In accordance to one or more aspects, cartridge 40 includes a passage 42 for disposing IERD 10. Passage 42 extends longitudinally from a first open end 68 to a second open end 69 of cartridge 40. Depicted cartridge 40 includes a nozzle 44 extending from the open end 69 of the cartridge to a nozzle tip 50. An injector 46 having a hollow body 70 is depicted extending from a proximal end 71 to a distal end 73 connected to the cartridge at first open end 68 such that a longitudinal lumen 72 extends from the proximal end 71 to nozzle tip 50. A plunger 48 is reciprocally positioned through proximal end 71.

IERD 10 is initially positioned in cartridge 40 in a decompressed state as illustrated for example in FIGS. 8 and 11. Depicted cartridge 40 includes a pair of cooperative panels 74, 76 that are slidably connected to one another by a frame 78. Each of the panels 74, 76 has a respective face side 80 that forms a groove 82, e.g. recessed portion of the face side, for disposing a portion of the IERD, for example for positioning the blade portions. The face sides 80 of the respective panels 74, 76 are oriented toward one another such that passage 42 is defined between the face sides. In the first position, see e.g., FIGS. 8, 11, panels 74, 76 are spread apart a distance such that IERD 10 can be positioned in passage 42 in the decompressed, expanded state. Panels 74, 76 have been moved toward each other in FIG. 9 to compress the IERD body between the respective face sides. FIGS. 9 and 12 illustrate cartridge 40 in a second position. Cartridge 40 may be held in the first position and the second position by connecting or locking mechanisms. For example, in FIGS. 11 and 12 each of the depicted panels 74, 76 have first locking elements 84 which are cooperative with second locking elements 86 of frame 78. In the illustrated example, first locking members 84 are protrusions, e.g., tabs, and second locking elements 86 are illustrated as recesses, such as dimples or slots, in which the protrusions are disposed to hold the cartridge in the respective first and second positions. The illustrated devices such as the locking element are merely examples and are not intended to be limiting.

IERD 10 is depicted in FIG. 8 in the decompressed state and cartridge 40 in the first position. For packaging and sterilization, cartridge 40 may be maintained in the first position holding IERD 10 in the decompressed state. The blades of the IERD are oriented such that two of the blades are aligned along the longitudinal axis of passage 42 of the cartridge and the other two blades are oriented along an axis perpendicular to passage 42. In preparation for use, the cartridge is moved to the second position compressing IERD 10 as illustrated for example in FIG. 9. At least one of panels 74, 76 and its face side is moved toward the side face of the other panel to compress the IERD body and place cartridge 40 in the second position. FIGS. 8 and 11 illustrate both of panels 74 and 76 spaced laterally away from the axis extending between openings 68, 69 such that both of the panels are moved toward one another to compress IERD 10 between the respective face sides. In accordance with aspects of the disclosure, in the first position, i.e. FIGS. 8 and 10, the side face of only one of the panels is spaced laterally away from the axis of the passage such that moving the panels or side faces together to compress the body entails moving only one of the panels toward the other panel.

As injector plunger 48 is advanced a viscoelastic 88 acts as hydraulic fluid to advance IERD 10 into cartridge nozzle 44 and during the medical procedure the IERD 10 and viscoelastic material will pass through nozzle tip 50. FIG. 10 illustrates IERD 10 positioned in nozzle 44 with feet 24 positioned at the bottom side of the nozzle. IERD 10 is compressed such that the blades of a circumferential pair of blades are positioned on opposite ends of the compressed and elongated body. For example, a proximal blade, identified as blade 20a, is located in nozzle 44 adjacent to injector 46 and a distal blade, identified as blade 20b, is positioned on the opposite end of the compressed body adjacent to the nozzle tip.

Figure 13:
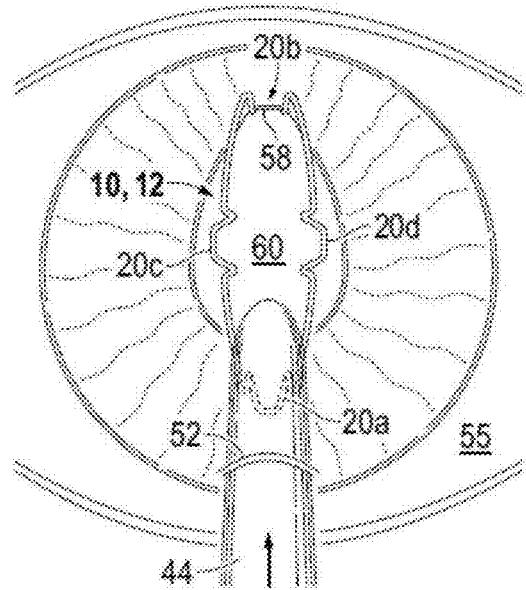
FIGS. 13 to 17 illustrate the insertion of an exemplary intraocular expansion and retention device into an eye in accordance to one or more embodiments.

An intraocular expansion and retention method is now described with reference to FIGS. 1-21. Body 12 of device 10 is compressed, elongated and positioned in a nozzle 44. Nozzle 44 is inserted through an incision 52, e.g., less than 3.2 mm, in cornea 54 (FIG. 17) of eye 55. Viscoelastic is injected into anterior chamber 56 (FIG. 17) and under iris margin 58. As illustrated in FIG. 13, the nozzle tip is positioned mid pupil, e.g., pupil opening 60, and the injector plunger is advanced thereby advancing IERD 10 through the nozzle tip into the eye. Intraocular tissue, for example iris margin 58 and/or capsule margin 57, distal from the incision 52 is disposed in the pocket 26 (FIGS. 2, 6) of the distal blade 20b as device 10 is advanced and the pupil opening 60 is elongated.

Figure 14:
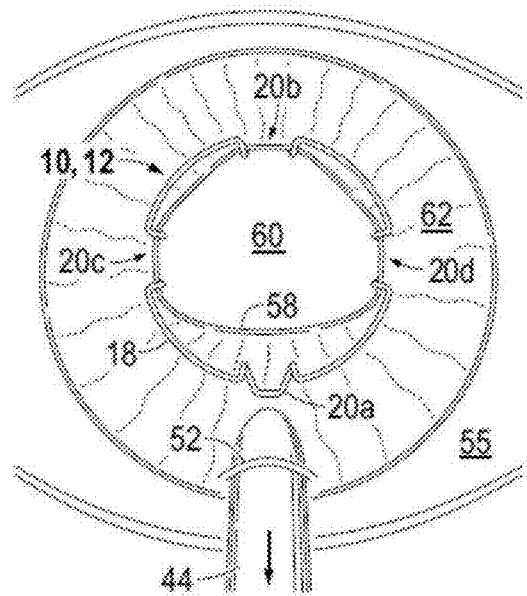

With reference to FIG. 14, injection continues while tilting the nozzle tip down and withdrawing the nozzle from incision 52 allowing the opposing lateral blades 20c and 20d to receive iris margin 58 as the body decompresses and expands. The proximal blade 20a, i.e. the foot of blade 20a, is laid on top of anterior iris 62. When IERD 10 exits the nozzle the compression bends expand top band 18 into a substantially circular shape. Cartridge nozzle 44 is removed from the anterior chamber through incision 52.

Figure 15:
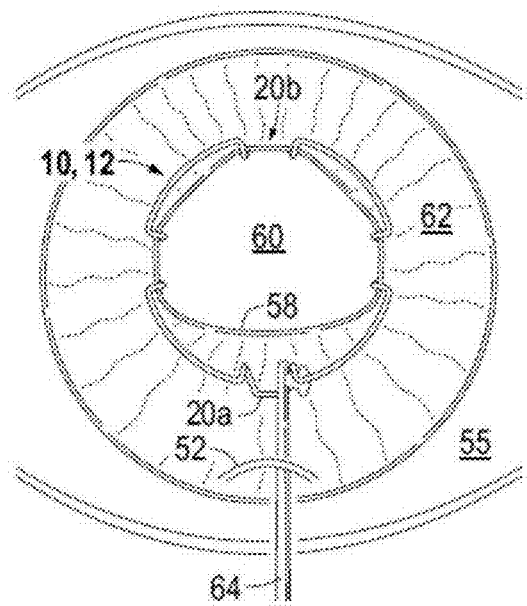

FIG. 15 illustrates the final blade, proximal blade 20a, being positioned on iris margin 58 using a manipulator 64. Manipulator 64 can grip a portion (e.g., leg or foot) of blade 20a and compress the body as needed to position the iris margin in the pocket of blade 20a. For example, the foot (i.e. feet 24) of the blade is positioned below the iris margin. As discussed above with reference to FIGS. 1-7, openings, e.g. gap 5, provide leveraging space for the instrument to manipulate blade 20, e.g., under the iris margin, to position the iris margin into pocket 26. Proximal blade 20a may be manipulated to be centered and aligned with incision 52, see FIG. 16, for later removal.

Figure 16:
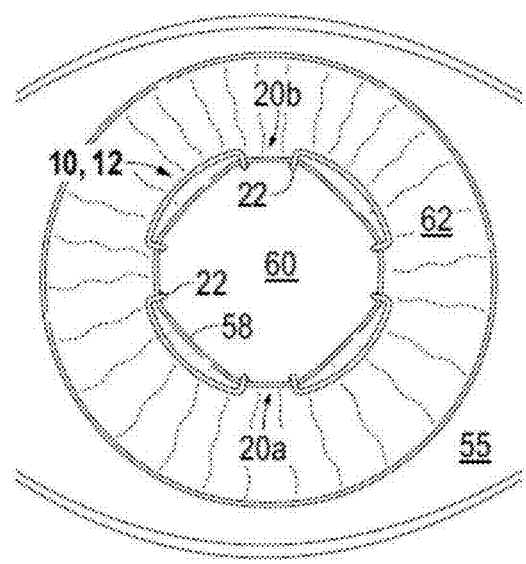

FIG. 16 illustrates IERD 10 centrally positioned with eight points of fixation on the iris margin 58. For example, the points of fixation being the points of contact between each leg 22 of the four blades and the iris margin. Device 10 creates a large circular pupillary opening 60 when in the decompressed, expanded state. For example, in FIG. 6, pupil opening 60 is symmetrically expanded beyond 7 mm.

Figure 17:
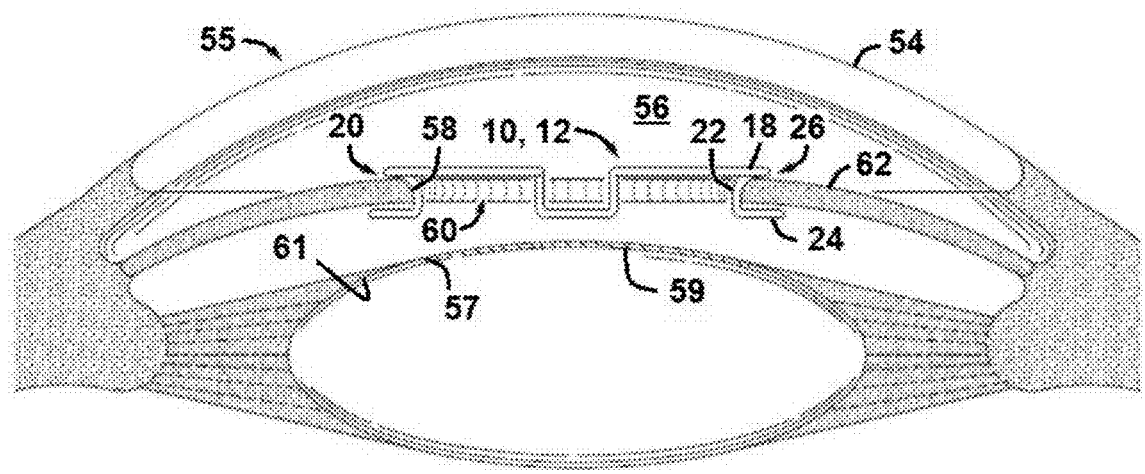
Figure 18:
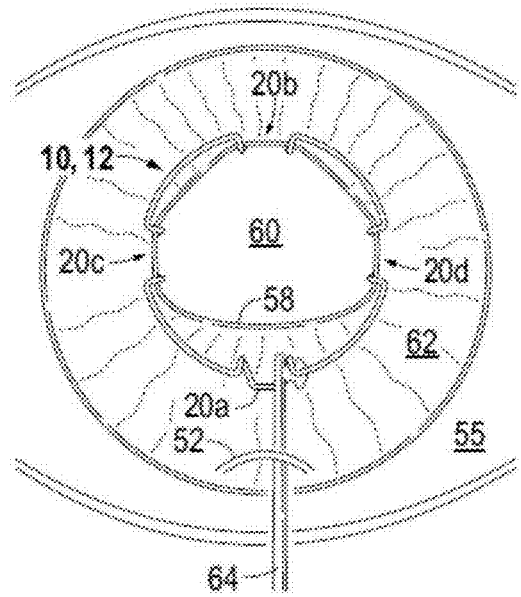
FIGS. 18-21 illustrate removal of an exemplary intraocular expansion and retention device from an eye in accordance to one or more embodiments.

FIG. 17 is a sagittal view of IERD 10 illustrating iris margin 58 cradled, e.g., cupped, in pockets 26 of blades 20. The height of pocket 26 provides for disposing the iris margin in the receptacle of the blade without damaging the iris tissue as occurs with clamping or wedging type devices. In some embodiments, IERD 10 engages margins 57 of a capsulorhexis 59 to retain and stabilize capsule 61 for example during cataract extraction procedures where zonular dehiscence, pseudo exfoliation or other indicators for use are present.

Figure 19:
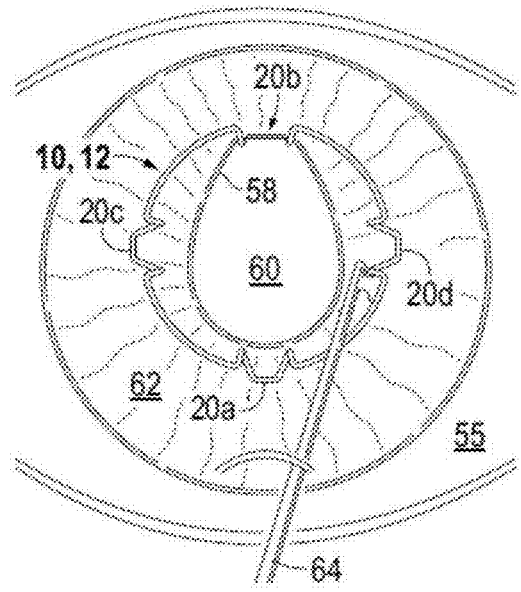
Figure 20:
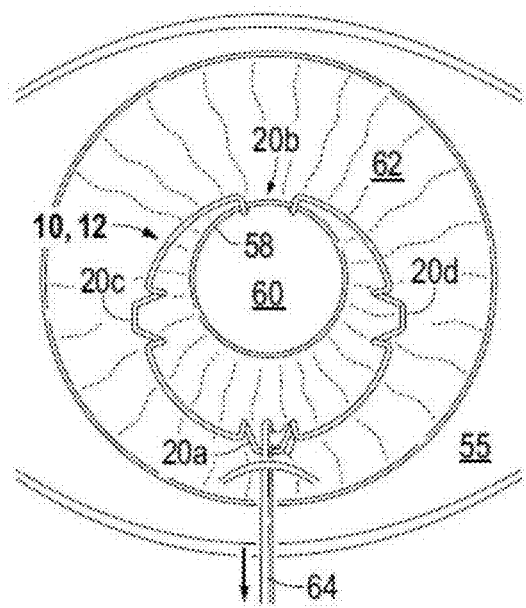
Figure 21:
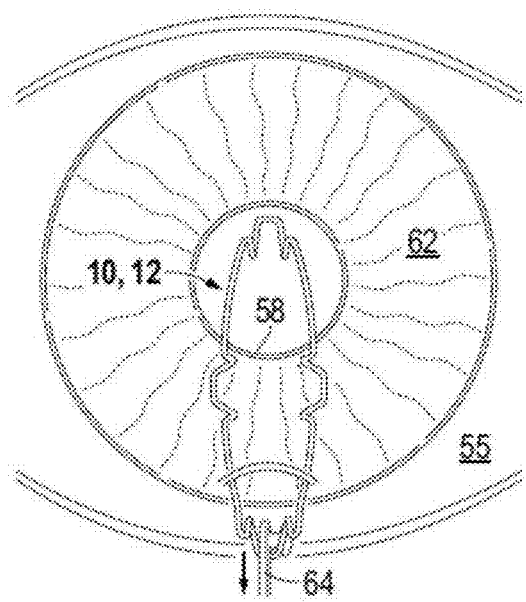

IERD 10 can be removed from the eye without cutting body 12. The removal process can be performed in a substantially reverse order of the insertion process. For example, with reference to FIGS. 18-21, an instrument such as manipulator 64 is inserted into the eye through incision 52. With the manipulator engaging IERD 10, proximal blade 20a is disengaged from the intraocular tissue by lifting the feet up and over the tissue, see FIG. 18. As illustrated in FIG. 19, the manipulator is used to disengage iris margin 58 from lateral blades 20c, 20d. With the proximal blade 20a and lateral blades 20c, 20d disengaged from the iris, proximal blade 20a may be gripped with the manipulator and IERD 10 drawn toward incision 52 as illustrated in FIG. 20. In FIG. 21, IERD 10 is drawn out of the anterior chamber of the eye through incision 52. The compressive force of eye tissue, e.g. the cornea, can compress IERD 10 as it is drawn through incision 52.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A method for expanding an intraocular opening to perform an intraocular procedure, comprising:
    compressing a circular circuitous body having a central opening with a center, a top band extending along a plane, and a first pocket, a second pocket, a third pocket, and a fourth pocket positioned vertically below the plane, wherein the pockets are equally spaced around the circular circuitous body, each of the pockets comprising the circuitous body extending inward from opposing top compression bends located at the top band toward the center to opposing top height bends, the circuitous body extending downward along legs, located radially inside of the top band, from the opposing top height bends to opposing bottom height bends, the circuitous body extending outward away from the center along feet from the opposing bottom height bends to opposing bottom compression bend, a front edge portion of the circuitous body connecting the opposing bottom compression bends, an inside diameter across the legs, an outside diameter across the top band, wherein the outside diameter is greater than the inside diameter, and an open gap in the plane between the opposing top height bends vertically above each of the pockets;
    inserting intraocular tissue in the first pocket of the compressed circuitous body;
    inserting the intraocular tissue into the second pocket and the third pocket of the compressed circuitous body, wherein the second and third pockets are located circumferentially opposite one another;
    decompressing the circuitous body into a circular shape before inserting the intraocular tissue in the fourth pocket; and
    inserting the intraocular tissue in the fourth pocket thereby expanding an opening in the intraocular tissue.

2. The method of claim 1, wherein the tissue comprises an iris margin.

3. The method of claim 1, wherein the intraocular tissue comprises a capsule margin.

4. The method of claim 1, wherein the circuitous body has eight points of fixation on the intraocular tissue when the intraocular tissue is inserted into all of the pockets; and
    the eight points of fixation are located radially inside of the top band.

5. The method of claim 4, wherein the tissue comprises an iris margin.

6. The method of claim 4, wherein the intraocular tissue comprises a capsule margin.

7. The method of claim 1, wherein the compressing comprises applying compression to the circular circuitous body of between about 2.3 grams and 7 grams of force.

8. The method of claim 1, wherein the intraocular opening is expanded from about 6 mm to 7.5 mm.

9. The method of claim 1, wherein the intraocular opening is expanded greater than about 7.5 mm.

10. The method of claim 1, wherein the circular body comprises eight points of fixation on the intraocular tissue when the intraocular tissue is inserted into all of the pockets and an inside diameter of the decompressed circular body across the points of fixation is about 6 mm or greater.

11. The method of claim 1, wherein the circular body comprises eight points of fixation on the intraocular tissue when the intraocular tissue is inserted into all of the pockets and an inside diameter of the decompressed circular body across the points of fixation is about 6.7 mm plus or minus ten percent.

12. A method, comprising:
using an intraocular expansion and retention device (IERD) to expand and maintain an intraocular opening in an expanded position during an intraocular procedure, the IERD comprising:
a circuitous body forming a central opening having a center, the circuitous body having a top band extending along a plane and spaced apart stepped blades, wherein each of the spaced apart stepped blades comprises opposing top compression bends located at the top band, the circuitous body extending from the opposing top compression bends inward into the central opening toward the center to opposing top height bends, the circuitous body extending downward away from the plane along legs from the opposing top height bends to opposing bottom height bends, the circuitous body extending outward from the center along feet from the opposing bottom height bends to opposing bottom compression bends, and a front edge portion of the circuitous body connecting the opposing bottom compression bends;
each of the stepped blades forming an outwardly facing pocket along the legs;
an inside diameter across the legs of the stepped blades;
an outside diameter across the top band, wherein the outside diameter is greater than the inside diameter; and
an open gap in the plane between the opposing top height bends above each of the pockets;
compressing the circuitous body;
inserting intraocular tissue defining the intraocular opening in the outwardly facing pockets of the compressed circuitous body; and
decompressing the circuitous body into a circular shape to thereby expand the intraocular opening.

13. The method of claim 12, wherein the inside diameter across the legs of the stepped blades is from about 6 mm to 7.5 mm when the circuitous body is decompressed into the circular shape.

14. The method of claim 12, wherein the inside diameter across the legs of the stepped blades is about 7 mm or greater when the circuitous body is decompressed into the circular shape.

15. The method of claim 12, wherein the inside diameter across the legs of the stepped blades is about 8 mm or greater when the circuitous body is decompressed into the circular shape.

16. The method of claim 12, wherein the circuitous body comprises an expansion force of not less than about 2.0 grams and not greater than about 7.0 grams to decompress the circuitous body into the circular shape; and
the inside diameter across the legs of the stepped blades is from about 6 mm to 7.5 mm when the circuitous body is decompressed into the circular shape.

17. The method of claim 12, wherein the circuitous body comprises an expansion force of not less than about 2.0 grams and not greater than about 7.0 grams to decompress the circuitous body into the circular shape; and
the inside diameter across the legs of the stepped blades about 7.5 mm or greater when the circuitous body is decompressed into the circular shape.

18. The method of claim 12, wherein the intraocular tissue comprises a capsule margin.

19. The method of claim 12, wherein the top compression bends and the bottom compression bends urge the intraocular tissue outward and expand the intraocular opening.

* * * * *